United States Patent [19]

Heveling et al.

[11] Patent Number: 5,714,610
[45] Date of Patent: Feb. 3, 1998

[54] PROCESS FOR THE PREPARATION OF 3-METHYLPIPERIDINE AND 3-METHYLPYRIDINE BY CATALYTIC CYCLIZATION OF 2-METHYL-1,5-DIAMINOPENTANE

[75] Inventors: Josef Heveling; Erich Armbruster, both of Naters; Walter Siegrist, Visp, all of Switzerland

[73] Assignee: Lonza Ltd., Basel, Switzerland

[21] Appl. No.: 525,744

[22] PCT Filed: Mar. 30, 1994

[86] PCT No.: PCT/EP94/01005

§ 371 Date: Nov. 2, 1995

§ 102(e) Date: Nov. 2, 1995

[87] PCT Pub. No.: WO94/22824

PCT Pub. Date: Oct. 13, 1994

[30] Foreign Application Priority Data

Apr. 2, 1993 [CH] Switzerland .............................. 1014/93
Jan. 6, 1994 [CH] Switzerland .................................. 37/94

[51] Int. Cl.$^6$ ........................ C07D 211/02; C07D 213/08
[52] U.S. Cl. ............................ 546/184; 546/252; 502/79; 502/415
[58] Field of Search ...................................... 546/184, 252; 502/79, 415

[56] References Cited

U.S. PATENT DOCUMENTS

| 3,903,079 | 9/1975 | Heinz et al. | 540/612 |
| 5,149,816 | 9/1992 | Goe et al. | 546/251 |
| 5,179,014 | 1/1993 | Watanabe et al. | 435/129 |
| 5,258,305 | 11/1993 | Yamada et al. | 435/280 |
| 5,334,519 | 8/1994 | Yamada et al. | 435/129 |

FOREIGN PATENT DOCUMENTS

| 0188316 | 8/1986 | European Pat. Off. |
| 0307926 | 3/1989 | European Pat. Off. |
| 755534 | 8/1956 | United Kingdom |
| 2165844 | 10/1985 | United Kingdom |
| WO 9000546 | 7/1989 | WIPO |
| WO 9000547 | 7/1989 | WIPO |
| WO 94/22824 | 10/1994 | WIPO |
| WO 95/32055 | 11/1995 | WIPO |

*Primary Examiner*—C. Warren Ivy
*Assistant Examiner*—Garth M. Dahlen
*Attorney, Agent, or Firm*—Fisher, Christen & Sabol

[57] ABSTRACT

In a process for preparing 3-methylpiperidine or 3-methylpyridine from 2-methyl-1,5-diaminopentane in the gaseous phase, the initial product is made to flow over catalysts. In the first step, 3-methylpiperidine is produced, and if required 3-methylpyridine is produced in a second step.

13 Claims, No Drawings

PROCESS FOR THE PREPARATION OF 3-METHYLPIPERIDINE AND 3-METHYLPYRIDINE BY CATALYTIC CYCLIZATION OF 2-METHYL-1,5-DIAMINOPENTANE

This application is a 371 of PCT/EP94/01005, Mar. 30, 1994.

The present invention relates to a process for the preparation of 3-methylpyridine (MPI) or 3-methylpyridine (PIC) from 2-methyl-1,5-diaminopentane (MPDA).

3-Methylpiperidine is used as a vulcanization accelerator and as an additive to lubricant oil. 3-Methylpyridine is used both as a solvent and as an intermediate in the preparation of nicotinic acid.

PCT application WO 90/00546 discloses the preparation of mixtures of 3-methylpiperidine and 3-methylpyridine starting from 2-methyl-1,5-diaminopentane by passing the gaseous starting material over a catalyst comprising metal oxides at 500°–600° C. Preferred catalysts are copper chromite, molybdenumoxide and vanadium oxide. These catalysts are preferably applied to a support. Depending on the reaction temperature, the ratio between piperidine and pyridine can be shifted to one or the other side. This patent specification also mentions the possibility of using acidic oxides, such as $SiO_2$ or silicon aluminium oxides, without further additives as catalysts. However, the yields achieved in this way are only moderate. No information is given on the catalyst activity over extended operating times.

U.S. Pat. No. 3,903,079 discloses a process for the cycloammonolysis of disubstituted alkanes containing primary amino and/or hydroxyl groups. The catalyst used is a metal aluminosilicate molecular sieve. Preferred metals are copper, palladium, manganese, nickel and chromium. The reaction is carried out in the presence of ammonia. The yields achieved are modest. A yield of 75% is achieved in the preparation of piperidine from 1,5-pentanediol.

The object of the present invention is to provide a process for the preparation of 3-methylpiperidine from 2-methyl-1,5-diaminopentane which can be carried out on a commercial scale and achieves high yields. The catalyst activity should be maintained over long times. A further object is to provide a process for the preparation of 3-methylpiperidine by further reaction of the 3-methylpiperidine over a dehydrogenation catalyst.

The object is achieved according to the invention by the process according to Patent claim 1.

The term "oxides of Al and/or Si" used in claim 1 is taken to mean the individual oxides, such as $Al_2O_3$, mixed oxides of $Al_2O_3/SiO_2$ and crystallized compounds thereof, such as aluminium silicates, in particular zeolites. It is important that they have a predominantly acidic character and a specific surface area of greater than 40 m$^2$/g. The acidic character arises from the ratio between acidic and basic centers on the surface, which must, in accordance with the invention, be greater than 2. The acidic centers are determined analytically by irreversible adsorption of $NH_3$ at 80° C., and the basic centres by irreversible adsorption of $CO_2$ at 80° C. Preferred catalysts for the novel process are activated $Al_2O_3$, mixed oxides of $Al_2O_3/SiO_2$, or zeolites. Zeolites are crystalline natural or synthetic aluminium silicates which have a highly ordered structure with a rigid three-dimensional network of $SiO_4$ and $AlO_4$ tetrahedra connected by common oxygen atoms. The ratio between the number of Si and Al atoms and oxygen is 1:2. The electrovalence of the aluminium-containing tetrahedra is compensated by inclusion of cations in the crystal, for example alkali metal or hydrogen ions. Cation exchange is possible. The spaces between the tetrahedra are occupied by water molecules before dehydration by drying or calcination.

If the zeolite, owing to its preparation method, is not in the catalytically active, acidic H form, but instead, for example, in the Na form, it can be converted fully or partially into the desired H form by ion exchange, for example with ammonium ions, followed by calcination or by treatment with acids.

The catalysts are preferably employed as fixed-bed catalysts, and the starting material is expediently passed through the catalyst using hydrogen or an inert gas, such as nitrogen, as carrier gas.

The reaction temperature is set at 300°–400° C., preferably at 305°–375° C. The pressure is 0–10 bar, preferably 0–5 bar above atmospheric.

A measure of the flow rate over catalysts is the mass hourly space velocity (MHSV). In the present case, an MHSV of 2.1–4.2 g of starting material per g of catalyst and per hour is advantageously maintained. The vapor-form starting material can be diluted, preferably with $N_2$ or $H_2$.

3-Methylpiperidine can be converted into 3-picoline by known dehydrogenation processes. The 3-methylpiperidine stream produced by the process of the invention can be passed directly over a dehydrogenation catalyst, so that the dehydrogenation takes place immediately after the cyclization. This is possible because the 3-methylpiperidine is produced in unusually high purity and in particular now contains virtually no MPDA, which has been found greatly to impair the activity of dehydrogenation catalysts.

The dehydrogenation catalysts used are preferably noble metals, such as, for example, Pd or Pt, on a support. Particularly advantageous dehydrogenation catalysts have been found to be those obtainable from amorphous silicon aluminium oxides by ion exchange with soluble palladium complexes, such as $[Pd(NH_3)_4]Cl_2$. The amorphous silicon aluminium oxides are advantageously first dewatered and charged with ammonia. The ion exchange with the soluble palladium complex can take place by suspension of the amorphous oxide in a solution of the complex. Alternatively, a solution of the complex can be passed through a packing of the amorphous oxide, but, in contrast to the former method, uniform loading can only be achieved by complete exchange.

The above methods also allow palladium contents of up to 5% by weight or more to be achieved in one step using relatively dilute solutions, for example 0.01 mol/l of $[Pd(NH_3)_4]Cl_2$.

The reaction temperature during the dehydrogenation is preferably 220°–400° C. In one embodiment, the cyclization catalyst is applied directly to the dehydrogenation catalyst bed, and the 2-methyl-1,5-diaminopentane is passed in from above. In a preferred embodiment, the catalysts are introduced into separate reactors. This allows independent temperature control and, if desired, independent catalyst regeneration.

The examples below illustrate the way in which the novel process is carried out. The pressures given in the examples are not absolute pressures, but excess pressures above atmospheric.

EXAMPLES 1–11

The examples shown in Table 1 below for the cyclization of methyldiaminopentane (MPDA) to methylpiperidine (MPI) were carried out as follows. Examples 1, 2 and 3 are comparative examples (not in accordance with the invention).

3 g of catalyst (particle size 0.32–1 mm) were introduced into a reactor (ø13 mm). MPDA was evaporated and passed over the catalyst with a 15 ml/min carrier-gas stream of N$_2$ at a pressure of 5 bar. The catalyst bed was heated in steps, and the reaction was monitored by gas chromatography. The more active the catalyst, the lower the temperature necessary for the cyclization of MPDA to MPI. The activity of the catalysts used can be compared with one another via the temperatures necessary for the highest possible MPI yield and taking into account the mass hourly space velocity.

The table is supplemented by characterization data on the catalysts used.

temperature of 335° C. The MHSV was 4.2 g of MPDA per gram of catalyst per hour. The MPDA used was a commercial product obtainable from Du Pont de Nemours under the trade name Dytek A. The experiment ran for 280 hours. Deactivation of the catalyst was not observed. The product was condensed, and the ammonia formed allowed to escape. The yields of MPI were virtually quantitative (>99.5%).

2nd Step: 10 g of a Pd-MgCl$_2$/Al$_2$O$_3$ dehydrogenation catalyst were introduced into a reactor (ø13 mm). The MPI from the previous experiment was passed in vapour form over the catalyst with a 15 ml/min carrier-gas stream of N$_2$ at a pressure of 1 bar and a temperature of 280° C. The MBSV was 0.23 g of MPI per gram of catalyst per hour. The

TABLE 1

MPDA to MPI:

| Example | Catalyst | T [°C.] | p [bar] | MHSV [g/(g · h)] | MPI [% in product] | BET surf. area [m$^2$/g] | Pore vol. [cm$^3$/g] | Average particle diameter [Å] | Acidic centres (A) [μmol/g] | Basic centres (B) [μmol/g] | A/B |
|---|---|---|---|---|---|---|---|---|---|---|---|
| 1 | Cu chromite | 380 | 5.0 | 2.1 | 13.3 | 120 | 0.37 | 113 | 203 | 0 | — |
| 2 | ZrO(OH)$_x$ | 350 | 5.0 | 2.1 | 6.5 | 240 | 0.25 | 32 | 150 | 99.5 | 1.5 |
| 3 | SiO$_2$ | 400 | 5.0 | 4.2 | 63.0 | 347 | 1.18 | 125 | 1400 | 1000 | 1.4 |
| 4 | Al-4405 E | 375 | 5.0 | 4.2 | 90.5 | 256 | 0.75 | 102 | no measurement | | |
| 5 | Al-3996 E | 350 | 5.0 | 2.1 | 89.0 | 211 | 0.74 | 116 | 165 | 52.5 | 3.1 |
| 6 | K-Y | 360 | 5.0 | 4.2 | 94.9 | | | | 800 | >150 | <5.3 |
| 7 | H-Y | 320 | 5.0 | 4.2 | 97.6 | | | | 2200 | 60 | 37.7 |
| 8 | H-Y | 325 | 5.0 | 4.2 | 97.6 | | | | | | |
| 9 | H-Y | 325 | 1.8 | 4.2 | 98.7 | | | | | | |
| 10 | Si-235-1 T | 320 | 5.0 | 4.2 | 99.3 | 376 | 0.5 | 47 | 156 | 1.6 | 97.5 |
| 11 | H-ZSM-5 | 305 | 5.0 | 4.2 | 99.6 | | | | 650 | approx. 90 | 7.2 |

Cu chromite: Cu-1230 R (Engelhard; 29% of Cu, 32% of Cr, 6% of Ba)
Al-4405 E: 97% of Al$_2$O$_3$ - 3% of SiO$_2$ (Engelhard)
Al-3996 E: Al$_2$O$_3$ (Engelhard)
K-Y: zeolite Y, K$^+$ - exchanged
H-Y: zeolite Y (Degussa)
Si-235-1 T: 87% of SiO$_2$ – 13% of Al$_2$O$_3$ (Engelhard)
H-ZSM-5: 54.5% of pentasil (Si/Al = 18) + 45.5% of binder

EXAMPLE 12

MPDA to 3-picoline:

4 g of a Pd catalyst (1% of Pd/Al$_2$O$_3$) were introduced into a reactor (ø13 mm) and covered by 3 g of H—ZSM-5. (The starting material was in all cases introduced into the reactor from the top). The working conditions were as follows: temperature 305°–320° C., 15 ml/min of N$_2$, pressure 5 bar. Yields of up to 97% of 3-picoline were obtained in the temperature range 305°–320° C. and at an MHSV of 0.6 g/(g.h), the only further product found being 2.9% of MPI. Complete conversion of the MPDA to the desired products thus occurred. No deactivation of the catalysts was observed over the course of 10 days. It is also possible to replace N$_2$ as carrier gas by H$_2$.

The novel procedure thus results in a significant improvement in the activity, selectivity and catalyst service life.

EXAMPLE 13

Preparation of 3-picoline using two separate reactors and commercial MPDA (MPDA to 3-picoline in 2 steps with isolation of MPI):

1st Step: 3 g of ZSM-5 in the ammonium form (particle size 0.5–1 mm) were introduced into a reactor (ø13 mm). MPDA was evaporated and passed over the catalyst with a 15 ml/min carrier-gas stream of N$_2$ at a pressure of 5 bar and a experiment ran for 190 hours. Deactivation of the catalyst was not observed. After 190 hours, the following product composition was determined by gas chromatography: 99.3% of 3-picoline, 0.4% of MPI.

EXAMPLE 14

Preparation of 3-picoline using two separate reactors and commercial MPDA (MPDA to 3-picoline in 2 steps without isolation of MPI):

3 g of NH$_4$-ZSM-5 (particle size 0.5–1 mm) were introduced into a reactor (ø13 mm). MPDA was evaporated and passed over the catalyst with a 15 ml/min carrier-gas stream of N$_2$ at a pressure of about 1 bar and a temperature of 320° C. The MHSV was between 1 and 2 g of MPDA per gram of ZSM-5 per hour. The MPDA used was a commercial product obtainable from Du Pont de Nemours under the trade name Dytek A. The product from the cyclization reactor was kept in the gas phase and passed directly to the second reactor. This reactor contained 12 g of a dehydrogenation catalyst having the composition Pd+MgCl$_2$ on an Al$_2$O$_3$ support (particle size 0.32–1 mm). The reaction conditions were 280° C. and about 1 bar. The condensate from the dehydrogenation reactor after a reaction time of 220 hours contained 99.1% of 3-picoline and 0.9% of MPI (according to gas chromatography). Deactivation of the two catalysts over the reaction time was not observed.

EXAMPLE 15

Comparative Example

Preparation of a 1% Pd/Al$_2$O$_3$ catalyst by impregnation:

6.3 g of Pd(NO$_3$)$_2$ hydrate (Heraeus) and 15.3 g of conc. HCl were added to 540 g of demineralized water. A pH of 0.7 became established. This solution was added to 250 g of Al$_2$O$_3$ (Al-4191 E 1/16" from Engelhard) which had been moistened in advance with demineralized water. The impregnation time was 3 days. The solution was subsequently decanted off and the catalyst was dried at 150° C. for 20 hours, then calcined at 550° C. for 2 hours in an air-circulation oven and granulated, and the sieve fraction from 0.315 to 1 mm was collected.

EXAMPLE 16

Comparative Example

Preparation of a 3% Pd/Al$_2$O$_3$ catalyst by impregnation:

Al$_2$O$_3$ (Al-3996 R from Engelhard) was granulated and the sieve fraction from 0.315 to 1 was used. Three impregnation solutions comprising 150 g of demineralized water, 1.8 g of Pd(NO$_3$)$_2$ hydrate (Heraeus) and 2.36 g of conc. HCl were prepared. A pH of approx. 0.8 became established. 70 g of the support were impregnated successively for 24 hours in each case with these three impregnation solutions; after each impregnation step, the catalyst was washed with 100 ml of demineralized water, dried at 150° C. for 2 hours in a vacuum oven and calcined at 550° C. for 2 hours in an air-circulation oven.

EXAMPLE 17

Comparative Example

Preparation of a 4% Pd/Al$_2$O$_3$ catalyst by impregnation:

Two impregnation solutions comprising 150 g of demineralized water, 1.25 g of Pd(NO$_3$)$_2$ hydrate (Heraesu) and 2.24 g of conc. HCl were prepared. A pH of 0.8 became established. 50 g of the catalyst from Example 2 were impregnated successively with these impregnation solutions; after each step, the catalyst was washed with 100 ml of demineralized water, dried at 150° C. for 2 hours in a vacuum oven and calcined at 550° C. for 2 hours in an air-circulation oven.

EXAMPLE 18

Preparation of a 5% Pd-SiO$_2$/Al$_2$O$_3$ catalyst by ion exchange with [Pd(NH$_3$)$_4$]$^{2+}$. The Si/Al oxide support (13% by weight of Al$_2$O$_3$) (Si-235-1 T from Engelhard) was granulated (0.315–1 mm). 50 g of the granules were dehydrated for 12 hours at 400° C. in a quartz tube in a stream of N$_2$. Dry ammonia gas (36 g) was passed over the cooled sample for 1 hour. A 0.01 molar [Pd(NH$_3$)$_4$]Cl$_2$ solution was prepared: 0.375 g of PdCl$_2$ were added to 100 ml of 0.84 molar aqueous NH$_3$ solution, and the mixture was stirred at 85° C. for 15 minutes. After cooling, the desired molarity was established by addition of water. 20 g of the pretreated support were stirred for 24 hours with 2542 ml of the 0.01 molar Pd salt solution. The catalyst was subsequently washed 6 times with 500 ml of demineralized water in each case and dried at 120° C. for 24 hours. The catalyst contained approx. 5% by weight of Pd.

EXAMPLE 19

Preparation of a 5% Pd-SiO$_2$/Al$_2$O$_3$ catalyst by ion exchange with [Pd(NH$_3$)$_4$]$^{2+}$:

150 g of the Si/Al oxide support (15% by weight of Al$_2$O$_3$) (Si-HP-87-069 T from Engelhard) were dehydrated for 12 hours at 400° C. in a quartz tube in a stream of N$_2$. Dry ammonia gas (60 g) was passed over the cooled sample for 1 hour. 70 g of the pretreated support were stirred for 20 hours with 3720 ml of a 0.01 molar Pd salt solution (prepared as described in Example 18). The catalyst was subsequently washed 6 times with 1000 ml of demineralized water and dried at 120° C. for 15 hours. The catalyst contained approx. 5% by weight of Pd.

EXAMPLE 20

Preparation of a 3% Pd-SiO$_2$/Al$_2$O$_3$ catalyst by ion exchange with [Pd(NH$_3$)$_4$]$^{2+}$:

120 g of the Si/Al oxide support (15% by weight of Al$_2$O$_3$) (Si-HP-87-069 T from Engelhard) were dehydrated for 12 hours at 400° C. in a quartz tube in a stream of N$_2$. Dry ammonia gas (35 g) was passed over the cooled sample for 1 hour. 35 g of the pretreated support were stirred for 24 hours with 1030 ml of a 0.01 molar Pd salt solution (prepared as described in Example 18). The catalyst was subsequently washed 6 times with 1000 ml of demineralized water and dried at 120° C. for 24 hours. The catalyst contained approx. 3% by weight of Pd.

EXAMPLE 21

Preparation of a 1% Pd-SiO$_2$/Al$_2$O$_3$ catalyst by ion exchange with [Pd(NH$_3$)$_4$]$^{2+}$:

76.5 g of the Si/Al oxide support (15% by weight of Al$_2$O$_3$) (Si-HP-87-069 T from Engelhard) were dehydrated for 12 hours at 400° C. in a quartz tube in a stream of N$_2$. Dry ammonia gas (69 g) was passed over the cooled sample for 1 hour. A 0.0033 molar [Pd(NH$_3$)$_4$]Cl$_2$ solution was prepared: 0.375 g of PdCl$_2$ were added to 100 ml of 0.84 molar aqueous NH$_3$ solution, and the mixture was stirred at 85° C. for 15 minutes. After cooling, the desired molarity was established by addition of water. 35 g of the pretreated support were stirred for 24 hours with 1030 ml of the 0.0033 molar Pd salt solution. The catalyst was subsequently washed 6 times with 1000 ml of demineralized water in each case and dried at 120° C. for 24 hours. The catalyst contained approx. 1% by weight of Pd.

EXAMPLE 22

Preparation of a 1% Pd-SiO$_2$/Al$_2$O$_3$ catalyst by treatment with PdCl$_2$:

150 g of the Si/Al oxide support (15% by weight of Al$_2$O$_3$) (Si-HP-87-069 T from Engelhard) were dehydrated for 12 hours at 400° C. in a quartz tube in a stream of N$_2$. Dry ammonia gas (60 g) was passed over the cooled sample for 1 hour. A 0.015 molar PdCl$_2$ solution was prepared analogously to Example 18. 35 g of the pretreated support were stirred for 24 hours with 1000 ml of the 0.015 molar PdCl$_2$ solution. The catalyst was subsequently washed twice with 500 ml of demineralized water and dried at 120° C. for 24 hours. The catalyst contained approx. 1.4% by weight of Pd; the chlorine content was below 0.01%.

EXAMPLE 23

Preparation of a 6% Pd-SiO$_2$/Al$_2$O$_3$ catalyst by ion exchange with [Pd(NH$_3$)$_4$]$^{2+}$ in a glass column:

900 g of the Si/Al oxide support (15% by weight of Al$_2$O$_3$) (Si-HP-87-069 T ⅛" from Engelhard) were dehydrated for 12 hours at 400° C. in a quartz tube in a stream of N$_2$. Dry ammonia gas (155 g) was passed over the cooled sample for 1.25 hours. 67.6 l of a 0.01 molar [Pd(NH$_3$)$_4$]Cl$_2$ solution were prepared: 119 g of PdCl$_2$ were added to 31.7 l of 0.84 molar aqueous NH$_3$ solution, and the solution was stirred at 85° C. until clear. After cooling, the desired molarity was established by addition of a further 35.9 l of water. The pretreated support was introduced into a glass column (length 115 cm, diameter 6.5 cm), and the Pd solution was circulated over the support for 15 hours by pumping (60 l/h) by means of a peristaltic pump. The catalyst was subsequently washed 6 times in a stirred vessel with 9 l of demineralized water in each case and dried at 120° C. for 24 hours in an air-circulation oven. The yellow catalyst (982 g) contained approx. 6% by weight of Pd.

EXAMPLE 24

Preparation of a 6% Pd-SiO$_2$/Al$_2$O$_3$ catalyst by ion exchange of an Si/Al oxide prepared by the sol-gel process with [Pd(NH$_3$)$_4$]$^{2+}$:

The Si/Al oxide powder (13% by weight of Al$_2$O$_3$) MS 13/110 from Grace was tableted (ø9 mm). The tablets were broken, and the screen fraction from 0.315 to 1 mm was collected. 95 g of the granules were dehydrated for 12 hours at 400° C. in a quartz tube in a stream of N$_2$ (250 ml/min). Dry ammonia gas (58 g) was passed over the quartz sample for 1 hour. 80 g of the pretreated support were stirred for 24 hours with 10.1 l of a 0.01 molar Pd salt solution (prepared as described in Example 18). The catalyst was subsequently washed 6 times with 1000 ml of demineralized water and dried at 120° C. for 24 hours. The catalyst contained approx. 6% by weight of Pd.

EXAMPLE 25

Preparation of a 2% Pd-ZSM-5 catalyst by ion exchange with [pd(NH$_3$)$_4$]$^{2+}$:

A pentasil zeolite (3.1% by weight of Al$_2$O$_3$) having a particle size of 0.315–1 mm contained 30% of aluminium oxide as binder. 60 g of the product were dehydrated for 12 hours at 400° C. in a quartz tube in a stream of N$_2$. Dry ammonia gas (35 g) was passed over the cooled sample for 1 hour. 20 g of the pretreated pentasil were exchanged with 420 ml of a 0.01 molar Pd salt solution (prepared as described in Example 18). The zeolite was subsequently washed 6 times with 250 ml of demineralized water and dried at 120° C. for 24 hours. The catalyst contained approx. 2% by weight of Pd.

EXAMPLES 26–33

Table 2

Dehydrogenation of 3-methylpiperidine (MPI) to 3-picoline (PIC):

3–10 g of catalyst (particle size 0.315–1 mm) were introduced into a reactor (ø13 mm). MPI was evaporated and passed over the catalyst at the reactor temperatures indicated in Table 2 (p=1 bar). In most cases, a 15 ml/min stream of hydrogen was additionally established.

The product stream was analysed by gas chromatography. The analysis values given in Table 2 were obtained after constant reaction conditions had become established (>20 hours):

TABLE 2

| | Catalyst | | | T | MHSV | PIC | MPI |
|---|---|---|---|---|---|---|---|
| Ex. | Type | Preparation | Addition | [°C.] | [l/h] | [GC area %] | |
| 26 | 1%Pd—MgCl/Al$_2$O$_3$ | DOS 3410542 | — | 270 | 0.25 | 93.6 | 4.3 |
| 27 | 1%Pd/Al$_2$O$_3$ | Example 15 | 15 ml/min H$_2$ | 280 | 0.44 | 97.0 | 2.4 |
| 28 | 4%Pd/Al$_2$O$_3$ | Example 17 | 15 ml/min H$_2$ | 270 | 0.44 | 98.8 | 1.2 |
| 29 | 5%Pd—SiO$_2$/Al$_2$O$_3$ | Example 18 | 15 ml/min H$_2$ | 280 | 1.76 | 99.3 | — |
| 30 | 3%Pd—SiO$_2$/Al$_2$O$_3$ | Example 20 | 15 ml/min H$_2$ | 280 | 1.76 | 99.2 | 0.3 |
| 31 | 1%Pd—SiO$_2$/Al$_2$O$_3$ | Example 21 | 15 ml/min H$_2$ | 280 | 1.76 | 98.4 | 0.2 |
| -"- | -"- | -"- | -"- | -"- | 0.88 | 99.0 | 0.2 |
| -"- | -"- | -"- | -"- | 290 | 0.44 | 99.5 | 0.2 |
| 32 | 1.4%Pd—SiO$_2$/Al$_2$O$_3$ | Example 22 | 15 ml/min H$_2$ | 280 | 1.76 | 57.8 | 40.6 |
| 33 | 6%Pd—SiO$_2$/Al$_2$O$_3$ | Example 24 | 15 ml/min H$_2$ | 280 | 1.76 | 99.3 | 0.3 |
| -"- | -"- | -"- | -"- | -"- | -"- | 98.4 | 1.2 |

It is striking that the impregnated Pd/Mg catalyst (Example 26) obtained in accordance with an earlier patent specification (DOS 3410542) and the catalysts obtained by impregnating aluminium oxide with Pd (Examples 27 and 28) give less 3-picoline and more unreacted MPI in the product stream than do the catalysts from Examples 15–17 and 19. This is all the more surprising since the experiments with the impregnated catalysts were carried out at a low mass hourly space velocity. The catalysts of Examples 29–31 and 33 were obtained by ion exchange of silicon/aluminium oxide with [Pd(NH$_3$)$_4$]Cl$_2$. The activity can be controlled to a certain extent via the degree of exchange (cf. Examples 29–31 with 5%, and 1% of palladium in the exchanged catalyst). Example 32 used a catalyst in which the support had not been treated with [Pd(NH$_3$)$_4$]Cl$_2$ but instead with PdCl$_2$. This catalyst exhibited a much lower activity than those treated with [Pd(NH$_3$)$_4$]Cl$_2$.

EXAMPLES 34–40

3–10 g of catalyst (particle size 0.315–1 mm) were introduced into a reactor (ø13 mm). The starting material used was a crude product ("MPI crude") prepared from a mixture of the following composition: 74.9% of MPI, 13.9% of 2-methyl-1,5-diaminopentane (MPDA), 5.1% of organic impurities (principally methylcyclopentane diamine) and 6.1% of water. The crude product was prepared by catalytic cyclization of the MPDA obtained in the starting mixture as in Examples 15–25. After the cylization, the "MPI crude" had the following composition: 89.9% of MPI, 4.0% of organic impurities and 6.1% of water. This starting material was evaporated and passed over the catalysts indicated in the table (p=1 bar) at the reactor temperatures shown in Table 3. In most cases, a 15 ml/min stream of hydrogen was additionally set up. The product stream was analyzed by gas chromatography.

format the outlet side, and the concentration gradient along the catalyst bed followed approximately an exponential function. The starting material had the following composition: 92.7% of MPI, 6.5% of water, 0.8% of organic impurities. The starting material was evaporated and passed over the catalyst bed (p=0.11 bar) at an MHSV of 4.73, based on the active catalyst (corresponding to 1 g of starting material per ml of catalyst bed per hour). The product stream was analysed by gas chromatography (GC area %). The conversion was quantitative, and after 339 hours the organic component of the product contained 99.3% of PIC and 0.7%

TABLE 3

| Catalyst | | | T | MHSV | PIC | MPI |
|---|---|---|---|---|---|---|
| Ex. | Type | Preparation | Addition | [°C.] | [l/h] | [GC area %] | |
| 34 | 1%Pd—MgCl/Al$_2$O$_3$ | DOS 3410542 | 15 ml/min H$_2$ | 280 | 0.44 | 96.0 | 0.2 |
| -"- | -"- | -"- | -"- | -"- | 1.76 | 84.5 | 10.1 |
| 35 | 5%Pd—SiO$_2$/Al$_2$O$_3$ | Example 18 | 60 ml/min NH$_3$ | 280 | 1.76 | 95.5 | 0.3 |
| 36 | 5%Pd—SiO$_2$/Al$_2$O$_3$ | -"- | — | 285 | 1.76 | 97.9 | " |
| -"- | -"- | -"- | — | -"- | 3.52 | 93.4 | 2.2 |
| 37 | -"- | -"- | 15 ml/min H$_2$ | 280 | 3.52 | 93.9 | 1.5 |
| 38 | 5%Pd—SiO$_2$/Al$_2$O$_3$ | Example 19 | 15 ml/min H$_2$ | 280 | 3.52 | 96.0 | 0.4 |
| 39 | 3%Pd—SiO$_2$/Al$_2$O$_3$ | Example 20 | 15 ml/min H$_2$ | 280 | 1.76 | 96.2 | 0.2 |
| -"- | -"- | -"- | -"- | 290 | -"- | 96.5 | 0.3 |
| 40 | 6%Pd—SiO$_2$/Al$_2$O$_3$ | Example 24 | 15 ml/min H$_2$ | 280 | 3.52 | 95.2 | 0.4 |

It is striking that the impregnated Pd-Mg catalyst (Example 34) obtained in accordance with an earlier patent specification (DOS 3410542) gives, at an MHSV of 1.76, less 3-picoline and more unreacted MPI in the product stream than do the catalysts from Examples 35–40. The catalysts of Examples 35–40 were obtained by ion exchange of silicon/aluminium oxide with [Pd(NH$_3$)$_4$]Cl$_2$. These catalysts have a considerably higher activity, and MPI conversions of greater than 99.5% can be achieved, even at an MHSV of 3.52.

The catalyst of Example 40 was obtained by ion exchange of a silicon/aluminium oxide prepared by the sol-gel process.

In Example 35, ammonia was metered in. The experiment shows that the ammonia liberated during the cyclization of MPDA to MPI does not interfere with the reaction. The reaction also proceeds when no hydrogen carrier gas is metered in (Example 36).

EXAMPLE 41

Pd-exchanged zeolite as catalyst:

10 g of the Pd-ZSM-5 catalyst from Example 25 (particle size 0.315–1 mm) were introduced into a reactor (⌀13 mm). MPI was evaporated and passed over the catalyst (p=1 bar) at a reactor temperature of 280° C. and an MHSV of 0.44. The product stream was analysed by gas chromatography (GC area %). After a reaction time of 21 hours, the product stream contained 99.2% of PIC and 0.8% of unreacted MPI. After a reaction time of 213 hours, the product stream contained 93.15% of PIC and 6.85% of unreacted MPI.

EXAMPLE 42

In this experiment, it was attempted to carry out the reaction isothermally. To this end, 27 g of the catalyst from Example 19 (particle size: 0.315–1 mm) were introduced into a reactor (⌀21 mm). The catalyst was diluted with 53 g of the catalyst support in such a way that the catalyst was diluted the most at the reactor inlet side, was in undiluted of organic impurities. Owing to the endothermicity of the reaction, a temperature of approx. 240° C. became established in the centre of the reactor (wall temperature 280°–300° C.). The temperature at the end of the catalyst bed was 300° C. over the entire reactor cross-section. After a reaction time of 362 hours, the starting material employed was pure, anhydrous MPI. After 454 hours, the product stream contained 99.2% of PIC, 0.4% of unreacted MPI an 0.4% of organic impurities.

EXAMPLE 43

2-Methyl-1,5-diaminopentane (MPDA) to 3-picoline continuously in 2 steps:

3 g of SiO$_2$/Al$_2$O$_3$ granules (Si-HP-87-069 T from Engelhard) in a particle size of 0.315–1 mm were introduced into a reactor (⌀13 mm). MPDA was evaporated and passed over the catalyst with a 15 ml/min carrier-gas stream of H$_2$ at a pressure of approx. 1 bar end a reactor temperature of 320° C., and was cyclized to MPI. The MPDA used was a commercial product obtainable from Du Pont de Nemours under the trade name Dytek A. The product from the cyclization reactor was kept in the gas phase and passed directly to a second reactor. This reactor contained 3 g of the dehydrogenation catalyst from Example 18 (particle size 0.32–1 mm). The reactor temperature was 280° C. and the pressure was 1 bar. During the experiment, the starting material was changed from MPDA to MPI and then to a crude product (3-MP crude) comprising a mixture having the following composition: 74.9% of MPI, 13.9% of MPDA, 5.1% of organic impurities (principally methylcyclopentanediamines) and 6.1% of water. The results with the corresponding MHSVs (MHSV based on reactor 1) are shown in Table 4 below:

Table 4:

| Starting material | MHSV [l/h] | PIC [GC area %] | MPI | Run time [h] | Deactivation [PIC %/h] |
|---|---|---|---|---|---|
| Dytek A | 2.1 | 99.7 | — | 71 | 0 |
| -"- | 3.15 | 99.6 | 0.2 | 25 | 0 |
| -"- | 4.2 | 98.6 | 1.4 | 48 | 0 |
| MPI | 4.1 | 95.2 | 3.8 | 3 | — |
| -"- | 3.52 | 98.6 | 0.6 | 92 | 0 |
| 3-MP crude | 4.2 | 93.9 | 1.5 | 170 | 0.0172 |

EXAMPLE 44

2-Methyl-1,5-diaminopentane (MPDA) to 3-picoline continuously in 2 steps:

3 g of SiO$_2$/Al$_2$O$_3$ granules (Si-HP-87-069 T from Engelhard) in a particle size of 0.315–1 mm were introduced into a reactor (ø13 mm). MPDA was evaporated and passed over the catalyst with a 15 ml/min carrier-gas stream of H$_2$ at a pressure of approx. 1 bar and a reactor temperature of 320° C., and was cyclized to MPI. The MPDA used was a commercial product obtainable from Du Pont de Nemours under the trade name Dytek A. The product from the cyclization reactor was kept in the gas phase and passed directly to a second reactor. This reactor contained 3 g of the dehydrogenation catalyst from Example 20 (particle size 0.315–1 mm). The reactor temperature was 280° C. and the pressure was 1 bar. During the experiment, the starting material was changed from MPDA to a crude product (3-MP crude) comprising a mixture having the following composition: 74.9% of MPI, 13.9% of MPDA, 5.1% of organic impurities (principally methyl-cyclopentanediamines) and 6.1% of water. The results with the corresponding MHSVs (MHSV based on reactor 1) are shown in Table 5 below:

TABLE 5

| Starting material | MHSV [l/h] | PIC [GC area %] | MPI | Run time [h] | Deactivation [PIC %/h] |
|---|---|---|---|---|---|
| Dytek A | 2.1 | 97.5 | 1.4 | 117 | 0.0204 |
| -"- | 1.0 | 98.2 | 0.7 | 18 | 0 |
| 3-MP crude | -"- | 97.6 | 0.2 | 119 | 0.0248 |

EXAMPLE 45

3-MP crude to 3-picoline, continuously in 2 steps with intermediate tar separator:

Compared with Example 44, the starting material had a different composition and a tar separator was installed between the 1st and 2nd reactors. 3 g of SiO$_2$/Al$_2$O$_3$ granules (Si-HP-87-069 T from Engelhard) having a particle size of 0.315–1 mm were introduced into a reactor (ø13 mm). The starting material was a crude product (3-MP crude) having the following composition: 45.8% of MPI, 29.9% of MPDA, 9.8% of organic impurities (principally methylcyclopentane-diamines) and 14.5% of water. The starting material was evaporated and passed through the reactor with a 15 ml/min carrier-gas stream of H$_2$ at an MHSV of 4.2 and at a pressure of approx. 1 bar and a reactor temperature of 320° C. The product from the cyclization reactor was passed through a tar separator (115° C.) and fed directly to a second reactor. This reactor contained 3 g of the dehydrogenation catalyst from Example 23 (particle size 0.315–1 mm). The reactor temperature was 280° C. After a reaction time of 335 hours, the organic phase of the product contained 94.6% of PIC and 5.4% of organic impurities (GC area %) with quantitative conversion of MPDA and MPI. Catalyst deactivation was not observed.

We claim:

1. A process for the preparation of 3-methylpiperidine from 2-methyl-1,5-diaminopentane in the gas phase, comprising passing gaseous 2-methyl-1,5-diaminopentane at a temperature of 300° to 400° C. and a pressure of from 0 to 10 bar above atmospheric pressure without addition of ammonia over a catalyst which is selected from the group consisting of activated Al$_2$O$_3$, an aluminum/silicon mixed oxide or a natural or synthetic zeolite, has a ratio between acidic centers and basic centers on the surface of greater than 2 and has a specific surface area of greater than 40 m$^2$/g, whereby 3-methylpiperidine is produced in a yield of at least 89 percent.

2. The process according to claim 1, wherein the reaction is conducted at a temperature of 305° to 375° C.

3. The process according to claim 2, wherein the catalyst is an aluminum/silicon mixed oxide.

4. A process for the preparation of 3-methylpyridine comprising (a) passing gaseous 2-methyl-1,5-diaminopentane at a temperature of 300° to 400° C. and a pressure of from 0 to 10 bar above atmospheric pressure without addition of ammonia over a catalyst whereby 3-methylpyridine is produced, said catalyst being selected from the group consisting of activated Al$_2$O$_3$, an aluminum/silicon mixed oxide or a natural or synthetic zeolite, has a ratio between acidic centers and basic centers on the surface of greater than 2 and has a specific surface area of greater than 40 m$^2$/g, whereby 3-methylpiperidine is produced in a yield of at least 89 percent, and (b) subsequently passing the 3-methylpiperidine over a second catalyst which is a dehydrogenation catalyst, whereby the 3-methylpyridine is produced.

5. The process according to claim 4, wherein the reaction in step (a) is conducted at a temperature of 305° to 375° C.

6. The process according to claim 5, wherein the catalyst in step (a) is an aluminum/silicon mixed oxide.

7. The process according to claim 4, wherein the dehydrogenation catalyst is a noble metal on a support.

8. The process according to claim 4, wherein the dehydrogenation is carried out at 220° to 400° C.

9. The process according to claim 8, wherein the dehydrogenation catalyst is a noble metal on a support.

10. The process according to claim 9, wherein the noble metal used is palladium or platinum.

11. Process according to claim 10, wherein the dehydrogenation catalyst used is palladium on an amorphous silicon/aluminum oxide prepared by ion exchange with a soluble palladium complex.

12. A process for the preparation of 3-methylpiperidine from 2-methyl-1,5-diaminopentane in the gas phase, comprising passing gaseous 2-methyl-1,5-diaminopentane at a temperature of 300° to 400° C. and a pressure of from 0 to 10 bar above atmospheric pressure without addition of ammonia over a catalyst which is selected from the group consisting of activated Al$_2$O$_3$, a natural zeolite and a synthetic zeolite, has a ratio between acidic centers and basic centers on the surface of greater than 2 and has a specific surface area of greater than 40 m$^2$/g.

13. A process for the preparation of 3-methylpyridine comprising (a) passing gaseous 2-methyl-1,5-diaminopentane at a temperature of 300° to 400° C. and a pressure of from 0 to 10 bar above atmospheric pressure without addition of ammonia over a catalyst whereby 3-methylpyridine is produced, said catalyst being selected from the group consisting of activated Al$_2$O$_3$, a natural zeolite and a synthetic zeolite, has a ratio between acidic centers and basic centers on the surface of greater than 2 and has a specific surface area of greater than 40 $m^2/g$, and (b) subsequently passing the 3-methylpiperidine over a second catalyst which is a dehydrogenation catalyst, whereby the 3-methylpyridine is produced.

* * * * *